United States Patent [19]

Deruyter et al.

[11] Patent Number: 5,698,772
[45] Date of Patent: Dec. 16, 1997

[54] METHOD AND DEVICE FOR DETERMINING DIFFERENT PHYSICAL PARAMETERS OF POROUS MATERIAL SAMPLES IN THE PRESENCE OF TWO-PHASE OR THREE-PHASE FLUIDS

[75] Inventors: Christian Deruyter; François Kalaydjian, both of Rueil-Malmaison, France

[73] Assignee: Institut Francais du Petrole, Rueil Malmaison, France

[21] Appl. No.: 607,429

[22] Filed: Feb. 27, 1996

[30] Foreign Application Priority Data

Feb. 27, 1995 [FR] France ................ 95 02342

[51] Int. Cl.[6] ........................... G01N 15/08
[52] U.S. Cl. ........................... 73/38; 73/152.07
[58] Field of Search ............... 73/38, 153, 152.07, 73/152.08, 152.09, 152.11

[56] References Cited

U.S. PATENT DOCUMENTS

| | | | |
|---|---|---|---|
| 2,345,935 | 4/1944 | Hassler | 73/38 |
| 2,437,935 | 5/1948 | Brunner et al. | 73/38 |
| 2,705,418 | 4/1955 | Reichertz et al. | 73/38 |
| 2,821,680 | 1/1958 | Slusser et al. | 73/38 |
| 4,537,063 | 8/1985 | Barnaby | 73/38 |
| 4,562,726 | 1/1986 | Barnaby | 73/38 |
| 4,669,299 | 6/1987 | Closmann | 73/38 |
| 4,679,421 | 7/1987 | Barree | 73/38 |
| 4,848,145 | 7/1989 | Blaschke et al. | 73/153 |
| 4,907,448 | 3/1990 | Giveens | 73/152.11 |
| 4,950,844 | 8/1990 | Hallmark et al. | 175/59 |
| 5,164,672 | 11/1992 | Gilliland et al. | 73/163 X |
| 5,263,360 | 11/1993 | Blauch et al. | 73/38 |
| 5,297,420 | 3/1994 | Gilliland et al. | 73/38 |
| 5,325,723 | 7/1994 | Meadows et al. | 73/152.11 |
| 5,341,101 | 8/1994 | Maerefat et al. | 73/153 X |
| 5,493,226 | 2/1996 | Honarpour et al. | 73/153 |

*Primary Examiner*—Hezron E. Williams
*Assistant Examiner*—Jay L. Politzer
*Attorney, Agent, or Firm*—Antonelli, Terry, Stout & Kraus, LLP.

[57] ABSTRACT

A sample S is placed in a rigid body 1 of a device, in a containment cell laterally delimited by a supple sheath 21 and, at the two opposite ends thereof, by two cell ends 13, 14. Channels (15, 16) in these ends communicate with the sample, by means of semipermeable membranes (17, 18), and with fluid circulation means including a pump (39) providing a first fluid (such as water), a column (28) for injecting a second fluid such as oil, two burets (33, 36) receiving the fluids displaced out of the sample and a supply assembly (43, 46) associated with valves, providing gas that can be applied to the injection column (28) in order to push the second fluid injected into the containment cell for measurements with three-phase fluids. The device and its method of operation can be used for studying geologic samples, for example.

9 Claims, 3 Drawing Sheets

METHOD AND DEVICE FOR DETERMINING DIFFERENT PHYSICAL PARAMETERS OF POROUS MATERIAL SAMPLES IN THE PRESENCE OF TWO-PHASE OR THREE-PHASE FLUIDS

FIELD OF THE INVENTION

The present invention relates to a method and to a device for determining different physical parameters of porous material samples in the presence of two-phase or three-phase fluids.

The method and the device according to the invention are suited for testing for example geologic samples and for determining different parameters such as the capillary pressure of rocks in drainage or imbibition phases, their wettability index, their relative permeability, their resistivity index, etc.

The device according to the invention notably applies to the petroleum sphere for determining the characteristics of rocks that have been taken from formations containing or likely to contain hydrocarbons.

The device also applies to civil engineering, for example, for the hydrology of grounds in order to appraise their degree of pollution for example, or to the building industry for testing building materials in order notably to decide on waterproofing treatments, for example.

BACKGROUND OF THE INVENTION

The saturation values that depend on parameters such as the wettability and the interfacial tension must be known at any point in order to determine the distribution of the oil and gas volumes in a reservoir or an aquifer. To that effect, the wettability of rocks with respect to the water and the oil that can be contained therein is determined. Rock drainage operations must therefore be carried out, i.e. a displacement of the fluids intended to decrease the water saturation, followed by imbibition operations, this term referring to a displacement of the fluids allowing the water saturation (Sw) of the rock to be increased. The capillary pressure at a point of a porous material containing two fluids in the continuous phase, one being a nonwetting fluid, the other a wetting fluid, such as oil and water for example, is defined, as it is well-known, as the difference Pc at equilibrium between the pressure P(oil) of the oil and the pressure P(water) of the water.

Different types of two-phase measurement devices are used to carry out laboratory drainage and imbibition operations. The sample bars are generally placed in a cell. At the opposite ends thereof, the cell comprises two ends communicating with means intended to establish a displacement of liquids under pressure through the sample tested. Measuring means are placed at different points along the bar in order to measure different parameters: pressures, local saturations measured by gammametry or scannography, electric resistivity, etc. The sample bar can be placed in an elastomer containment sheath compressed by an injection of fluid under pressure.

Different two-phase measurement devices for measuring physical parameters of porous solid samples are described for example in the patent applications FR-2,603,040, EN.93/09,481, EN.94/10,783 and EN.94/15,546, or in patents U.S. Pat. Nos. 4,868,751; 5,506,542 and 5,069,065.

SUMMARY OF THE INVENTION

The measuring system according to the invention is suited for carrying out measurements on material samples by displacing therethrough two-phase fluids consisting of a wetting liquid such as water, for example, and of a nonwetting liquid such as oil for example, as well as three-phase fluids by completing these liquids with a gas.

The improved knowledge of different parameters characteristic of rocks and notably of their wettability for example, which is provided by these three-phase fluid displacement laboratory tests, notably allows to determine in an optimum way the nature of the fluids, such as water and gas, to be injected into a petroliferous formation in order to drain the effluents it contains, within the scope of enhanced recovery operations.

The device according to the invention includes a sample containment cell that is delimited by at least one rigid tubular sleeve and two cell ends at its two opposite ends, means for fastening each end to the tubular sleeve, an elastic sheath inside the cell, where the sample is placed, both cell ends being provided with an end part suited for fitting into the sheath at the opposite ends thereof and with channels communicating with means intended to provide a displacement of fluids under pressure through the sample, and pressure means for pressing the sheath radially against the sample.

The device is characterized in that each cell end comprises a removable cover of a smaller section than the end part of each cell end, allowing to get to the opposite ends of the sample during operation, the sheath being pressed against the sample by the radial pressure means.

Another feature of the device lies in that each tubular part comprises at least one radial extension provided with a radial bore, and means for establishing a connection through this extension between the inside of the elastic sheath and a gas supply assembly.

Another feature of the device lies in that the means intended to obtain a displacement of fluids under pressure through the sample include two fine tubes respectively connected to the two opposite ends of the sample through the two cell ends so as to collect said two phases displaced out of the sample, means for injecting these two phases, communicating respectively with the two opposite ends of the sample, comprising a pump and an injection column, and in that the gas supply assembly includes a first circuit provided with control means for delivering gas under controlled pressure at the two opposite ends of the two fine tubes, and a second circuit provided with control means for applying gas under pressure to the injection column so as to inject one of the fluid phases into the containment cell, and means for measuring pressure differences between different phases.

Another feature of the device lies in that the gas supply assembly comprises a third circuit provided with control means for injecting gas into the containment cell through at least one radial extension, for measurements in connection with three-phase fluids, the means for measuring pressure differences between phases include a differential pressure detector and multiple-way control means for connecting selectively said detector to two of the three circuits.

Another feature of the device lies in that the gas supply assembly also includes an injection pressure regulating element and a saturator containing liquid.

Another feature of the device lies in that it includes a processing assembly for co-ordinating the circulation of the different phases through the sample and the different circuits.

Another feature of the device lies in that it includes semipermeable membranes that can be interposed between at least one of the cell ends and one end of the sample.

The invention also relates to a method for studying a more or less porous material sample, in order to determine different physical parameters in connection with a wetting fluid, a nonwetting fluid and a gas, comprising using a sample in a containment cell as defined above, that comprises carrying out stages of drainage of the wetting fluid by the nonwetting fluid until an irreducible saturation is reached, followed by imbibition stages with the wetting fluid until a determined saturation degree is reached, characterized in that it comprises raising the pressure of the nonwetting fluid while maintaining the saturation degree reached until a determined capillary pressure is obtained, and injecting gas by successive increments so as to obtain a displacement of the nonwetting fluid by the gas in the presence of the wetting fluid.

The device according to the invention and its implementation method are advantageous on several accounts:

- the passage from two-phase fluid displacement operations to three-phase fluid displacements is facilitated by the covers that can be removed without dismantling the cell and that allow the function of the semipermeable membranes to be changed as the case may be,
- the distribution circuits and the control valves allow two-phase as well as three-phase measurement operations to be performed. This is notably the case for the gas that can be directed either towards the injection column for pushing the oil, or directly towards the peripheral inlets in order to be injected into the sample, within the scope of three-phase measurement operations.

BRIEF DESCRIPTION OF THE DRAWINGS

Other features and advantages of the method and of the device according to the invention will be clear from reading the description hereafter of embodiments given by way of non limitative examples, with reference to the accompanying drawings in which.

DESCRIPTION OF THE PREFERRED EMBODIMENTS

The device is suited for carrying out measurements on more or less porous material samples, notably rock samples, that are placed in a containment cell similar to that defined and shown in detail in the above-mentioned patent application EN.94/15,546.

Figure 1:
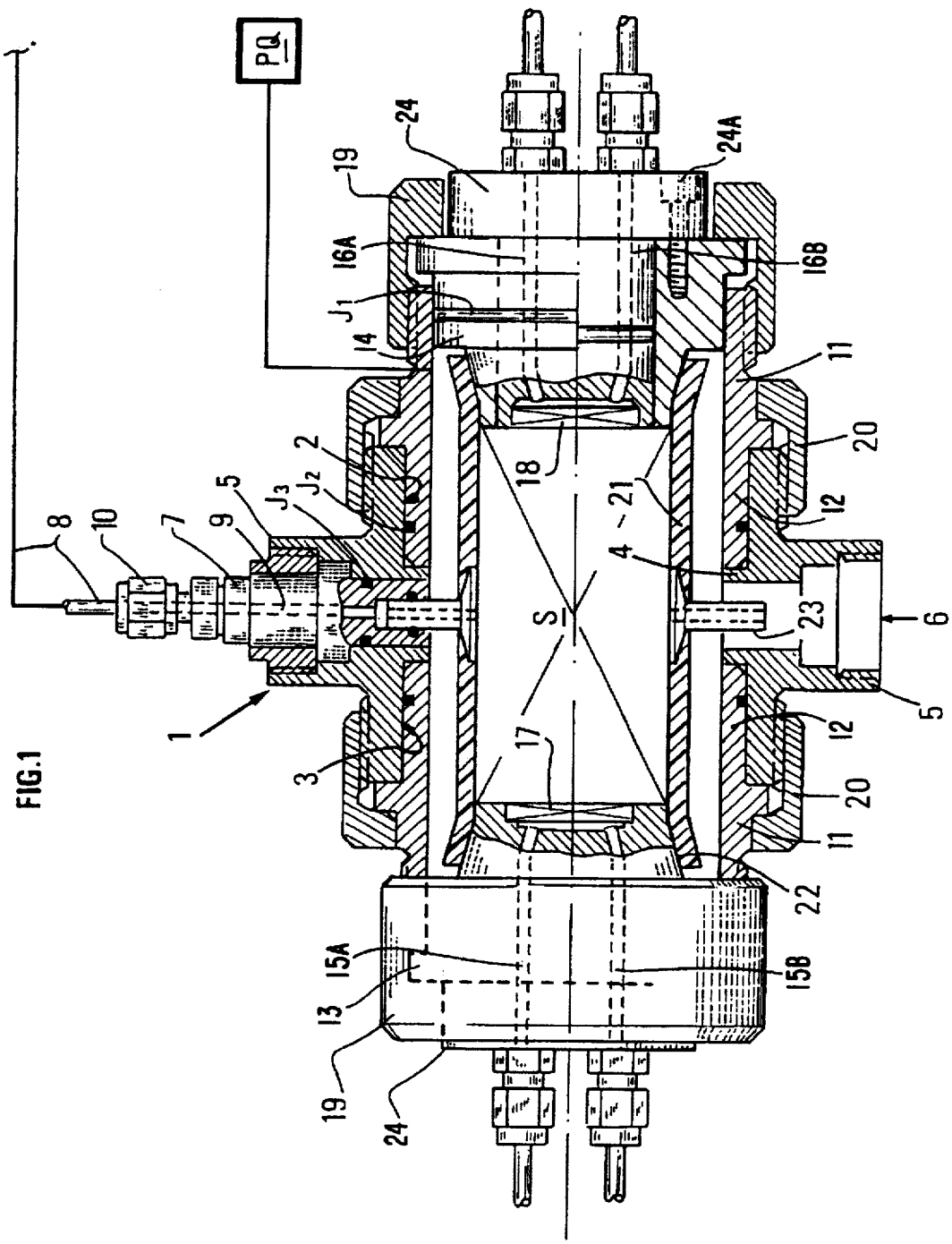
FIG. 1 shows the cell intended for the circulation of two-phase or three-phase fluids through a sample.

According to the embodiment of FIG. 1, the device includes a tubular connecting sleeve 1 provided with two cylindrical cavities 2, 3 on either side of a central shoulder 4. The sleeve comprises for example two radial extensions 5, the second forming the continuation of the first one, provided each with a central bore 6 in which the joining piece 7 of a tube 8 can be screwed. This radial joining piece 7 comprises for example a needle valve 9. It can be actuated by the rotation of a ring 10 and communication with tube 8 can be controlled thereby.

The device also includes two end stop rings 11 provided each with a tubular extension 12 suited for fitting into the cavities 2, 3 of each connecting sleeve 1. At each end, the device comprises a cell end 13, 14 crossed right through by two channels 15A, 15B, 16A, 16B to which membranes 17, 18 linked with fluid circuits (described hereafter) can be connected.

Semipermeable membranes 17, 18 of variable thickness can be possibly interposed between the sample S to be tested and the two ends 13, 14. These membranes are pressed against the porous sample S so as to ensure good capillary continuity. They are selected as a function of the fluids to be displaced in the sample.

A threaded ring 19 suited for being screwed onto an end stop ring 11, so as to cause each of the cell ends 13, 14 to rest against an end face of the sample S, is fastened to each cell end. Another threaded ring 20 immovably fastened in rotation to each stop ring allows the tubular extensions 12 of stop rings 11 to fit into the bottom of the cavities in sleeve 1.

In order to exert a radial pressure on sample S, the latter is placed in an elastic sheath 21. Each of the cell ends 13, 14 comprises a truncated end part suited for fitting under the sheath at each end thereof so as to delimit a containment cell therewith. The annular space around sheath 21 is in communication with means PQ delivering a fluid under pressure by means of a line connected to a port (not shown). The joining piece 7 fastened to each radial extension 5 along the axis thereof comprises a housing for a rigid eyelet 23 crimped through sheath 21 so as to communicate the sample S contained therein with line 8.

Each of the ends 13, 14 is preferably provided, along the longitudinal axis thereof, with a removable cover 24 that can be removed at will in order to free the sample ends. Each cover 24 is fastened to the corresponding cell end by screws 24A. This layout facilitates the setting or the changing of the membranes that may be necessary either because they have been damaged while being set at the ends of the sample, or for the purpose of the tests performed, as shown in the functional description hereafter.

The sample remains in place, immobilized by the sheath 21 by which the example is shut in, and subjected to a radial pressure. The ongoing tests are practically not disturbed. This is useful notably when the cell containing the sample is to be analyzed in a scannograph or in a gammameter in order to determine the local saturations of the sample. The precise measurement locations that are associated with the different images provided by these apparatuses remain valid, which facilitates comparisons and therefore allows to follow the image modifications during the fluid displacement processes.

The first channel 15A through cell end 13 communicates with a line 25 that is connected, by a first end, to a first inlet of two two-way valves 26, 27 and, by its other end, to a column 28 for injecting a nonwetting fluid such as oil by means of a valve 29. The second channel 15B through cell end 13 communicates with a line 30 connected, by means of a gas detector 31 of the optoelectronic type, for example, and of a valve 32, to a first end of a first glass tube or buret 33 whose inside diameter is calibrated. Gas detector 31 is used to detect possible gas escapes.

The first channel 16A through the opposite cell end 14 communicates with a line 34 connected by a valve 35 to a first end of a second buret or column 36. The second channel 16B communicates with a line 37 connected, by means of a valve 38, to a pump 39. Line 37 is also connected to a second inlet of the two-way valve 27 by means of a line 40.

The opposite ends of the two burets 33, 36 communicate, by means respectively of two valves 41, 42, with an enclosure 43 containing gas under pressure. The pressures prevailing in the burets 33, 36 are measured respectively by two detectors 44, 45 placed at the respective bases thereof.

The respective heights of the fluids in the two tubes 33, 36 are measured by physical detectors of a well-known type that are not shown. It is therefore possible, knowing the inside diameter of the glass tubes and the density of the fluid, to deduce easily the volumes of fluid collected as a function of time, as well as the mean saturations of the phases as a function of the pore volume of the sample.

The device includes means for delivering a gas under controlled pressure, comprising a pressurized gas tank 46, a pressure regulator 47 delivering gas as a function of a set pressure value, a saturator 48 containing oil and water, through which flows the gas coming from regulator 47.

Saturator 48 is connected to a line 50 by means of a valve 49A. This line supplies the opposite end of injection column 28 with gas and it communicates with a line 52 by means of a valve 51A. Line 52 is connected on the one hand to a second inlet of the two-way valve 26 and, on the other hand, to two lines 8 controlled each by a needle valve 9 (FIG. 1) and connected to the radially opposite extensions 5 of connecting sleeve 1. Line 52 can also be communicated with another pressurized gas source (not shown) by means of a valve 51B. An escape valve 49B allows a pressure decline of the gas to be controlled in line 50 if need be.

A plastic float 53 whose gravity is slightly lower than that of the nonwetting fluid is interposed between it and the gas. It allows the diffusion of the driving gas in the nonwetting fluid to be prevented.

The respective pressures of the oil and of the gas in injection column 28 are measured by two pressure detectors 54, 55 communicating respectively with the opposite ends thereof.

A differential detector 56 is placed between the respective third inlets of the two-way valves 26, 27 in order to measure, according to the channels supplied, the difference between the pressures of two of the fluids.

Figure 2:
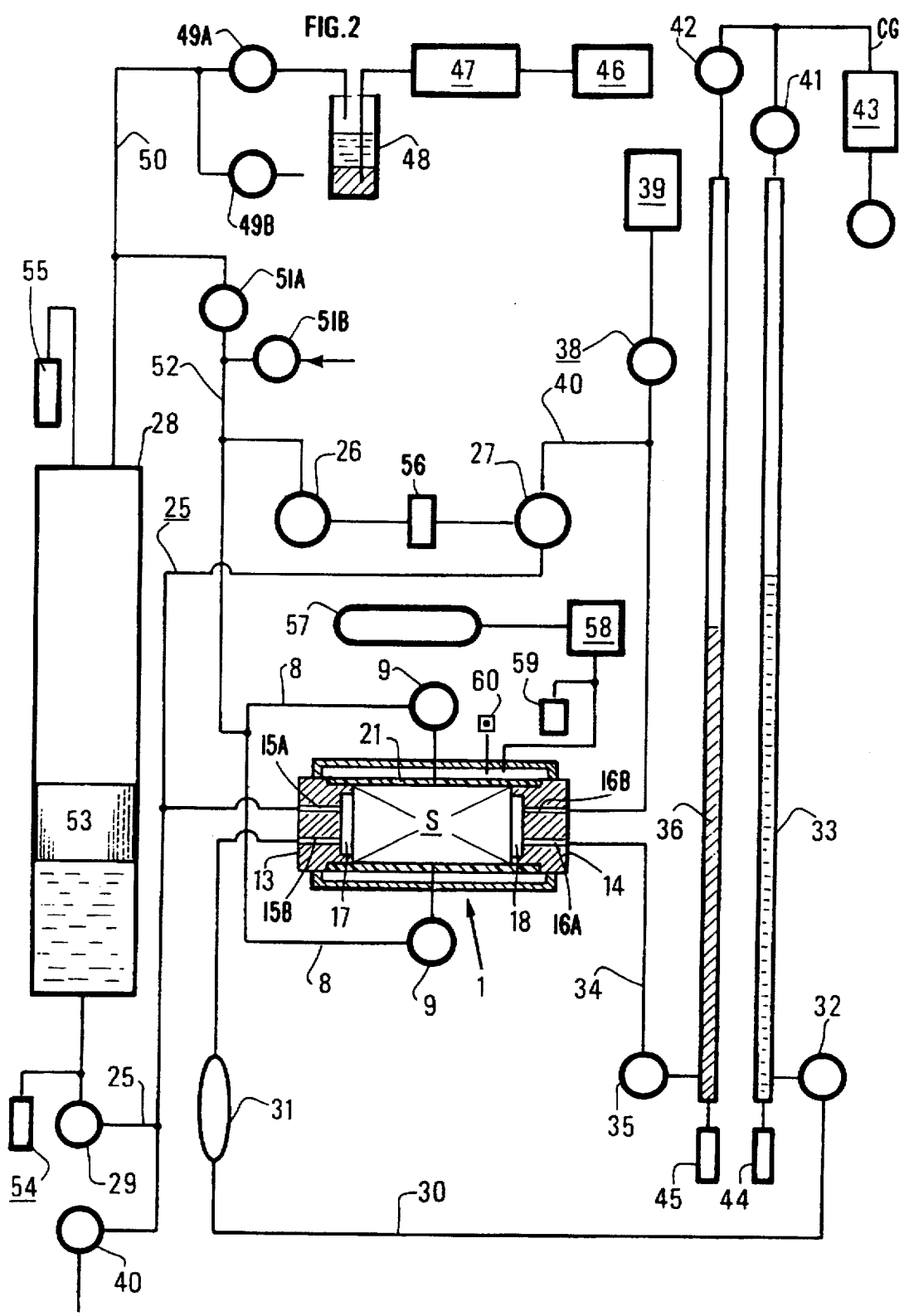
FIG. 2 shows the fluid distribution circuits associated with the cell.

The means PQ (FIG. 1) delivering a fluid under pressure include (FIG. 2) a pressurized oil tank 57, a nonreturn valve 58 and a pressure detector 59.

By means of another radial extension, not shown, like extension 5 for example (see FIG. 1 ), the sheath 21 containing the wall of the sample communicates with a pressure detector 60.

Figure 3:
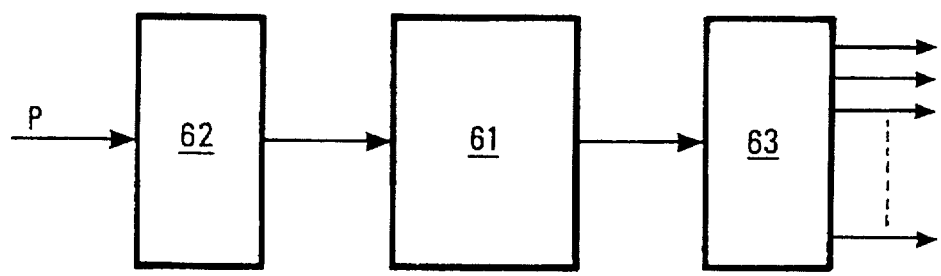
FIG. 3 is a flowsheet of a control system.

The device further includes (FIG. 3) a processing assembly comprising a programmed microcomputer 61, an acquisition card 62 for acquiring the pressure measurements performed permanently by the different pressure detectors, and a control assembly 63 for controlling selectively the different valves. The softwares associated with microcomputer 61 are suited for controlling the processes described hereafter.

Prior to any measuring cycle

The cylindrical porous sample S, washed, dried and weighed, is placed in the cell inside sheath 21 and a confining pressure is applied thereto. The porous sample thus prepared is placed in a dry state in a two-energy scanner (not shown). It is thereafter vacuum saturated in a desiccator with a wetting fluid which is loaded with an X-ray absorbing or a gamma ray absorbing salt and which does not notably modify the density of the sample. The sample is weighed after the saturation. The difference between the dry weight and the saturated weight, divided by the density, gives the value of the pore volume as well as the porosity, knowing the dimensions of the sample.

Circuits 25 and 37 are saturated with water by means of pump 39. Valve 32, gas detector 31 and needle valves 9 are closed. The sample is scanned again in order to determine its porosity and the maximum wetting fluid saturation. The permeability of the sample is determined by injecting water by means of pump 57 and by measuring the pressures by means of pressure detectors 59, 60 at different flow rates in order to check the linearity of Darcy's law.

Cell ends 13, 14 are dismounted in order to set the semipermeable membranes that are suitable for the experimentation. For three-phase fluid measurements for example, a pile or stack of semipermeable membranes whose combined effects allow passage of oil but stop water and gas is placed near to the end 13. Membranes allowing passage of liquids but not of gas are placed near to the end 14.

Injection column 28 is filled with nonwetting fluid. Circuit 25, end 13, valves 29, 32, gas detector 31 and buret 33 are oil-saturated. Pressure detector 54 measures the fluid injection pressure during the drainage or the imbibition. Pressure detector 55 measures the pressure of the driving gas. Circuit 37, end 14, valve 35 and buret 36 are water-saturated. Pressure detectors 44, 45 measure the respective heights in the burets 33, 36 in which the water or the oil is recovered and the volume of each phase recovered is deduced therefrom. The differential pressure detector 56 measures the pressure difference between the different phases: oil-water, gas-oil, gas-water, according to the selected channels.

Measuring cycles

The device allows all the following operations to be performed:

oil-water two-phase drainage, water-oil two-phase imbibition, relative permeabilities, gas-oil-water three-phase drainage (mobile or irreducible), water-oil three-phase imbibition, three-phase relative permeabilities.

Two-phase measurements

Drainage

The two-phase drainage of the sample is obtained by means of the displacement, by progressive pressure stages, of the wetting phase by the nonwetting phase. The cell is placed with end 13 upwards so as to avoid the segregation effects due to gravity.

The purpose of this operation is to plot the curve of the differential pressure between the wetting fluid and the nonwetting fluid as a function of the nonwetting fluid saturation. The two-way valve 26 is set to the oil position and the two-way valve 27 to the water position. The differential pressure measured by pressure detector 56 will be the pressure difference between the wetting phase and the nonwetting phase.

Valves 38, 9, 32 are closed. A gas pressure, applied and controlled by regulator 47, measured by pressure detector 55, pushes float 53. The oil running through valve 29, circuit 25, end 13 and membranes 17 displaces the water contained in the sample, which flows out through end 14, through membranes 18, up to a certain volume imposed by the capillary pressure. The effluents are recovered in buret 36 and the height of water is measured by pressure detector 45. The differential pressure measured by detector 57 is maintained permanently constant by a regulation system that includes regulator 48, exchanger 49, valves 49A, 49B and 51.

If an incident occurs: pressure decline or overpressure for example, valve 35 allows buret 36 to be isolated. The acquisition assembly 62 controlled by microcomputer 61 records, at time lapses chosen by the operator, the different physical measurements: pressures, volumes, possible anomalies. When the production of water stops, the porous sample is scanned in order to determine the saturations of the two phases. A new pressure stage can then be established. Gas is injected by controlling valve 51B. The pressure of regulator 47 is readjusted so as to obtain a gas flow rate satisfying the maintenance of the desired new differential pressure measured by detector 56. The progressive pressure stages are stopped when the hydrophilic membranes allow passage of the oil phase.

At each pressure stage, microcomputer 61 displays, on the control screen, the curve Pc=f(nonwetting fluid saturation) as well as the relative permeability curves. The irreducible or desired saturation is reached for a given capillary pressure.

Determination of the relative permeabilities is obtained indirectly by analyzing the displacement of a fluid by another.

Imbibition

The imbibition operations can be performed by lowering the pressure by regular stages, by means of valve 51B, and by checking that the saturation is really stable. The different phases are similar to those described for the drainage.

Three-phase operations

Drainage

The cell is adjusted to three-phase operations by withdrawing the cover 24 from end 14 in order to add an oleophilic membrane thereto.

The following stages have to be carried out in order to obtain a curve of drainage capillary pressure in the presence of a mobile or non-mobile water:

saturation of the porous medium with water, plotting the water-oil drainage capillary pressure curve (plot $C_1$, on FIG. 4) up to a pressure giving the desired irreducible saturation SWi, lowering the pressure in the oil so as to obtain a water reimbibition until a determined water saturation Sw is obtained along plot $C_2$ (FIG. 4), three-phase drainage by injecting gas by progressive pressure stages in order to displace the oil.

The three-phase drainage capillary pressure is defined by Pc=Pg–Po, where Pg is the gas pressure and Po the oil pressure. Po is expressed by the relation $$Po=Pw+fd(Sw) \qquad (1)$$

where Pw is the water pressure (the atmospheric pressure in practice) and fd(Sw) the oil/water drainage curve, and not by the relation Po=Pw+fi(Sw) where fi(Sw) is the oil/water imbibition curve. This is due to the fact that, by repressurizing the sample in the cell, during the drainage operation with gas, the circulation of the two fluids oil and water is restored in the direction of a drainage. Since the capillary pressure was that of point A (plot $C_1$) at the end of the imbibition, the oil pressure has to be raised in order to have the representative point at B on plot $C_2$, before beginning to inject gas by successive increments in order to displace the oil.

Figure 4:
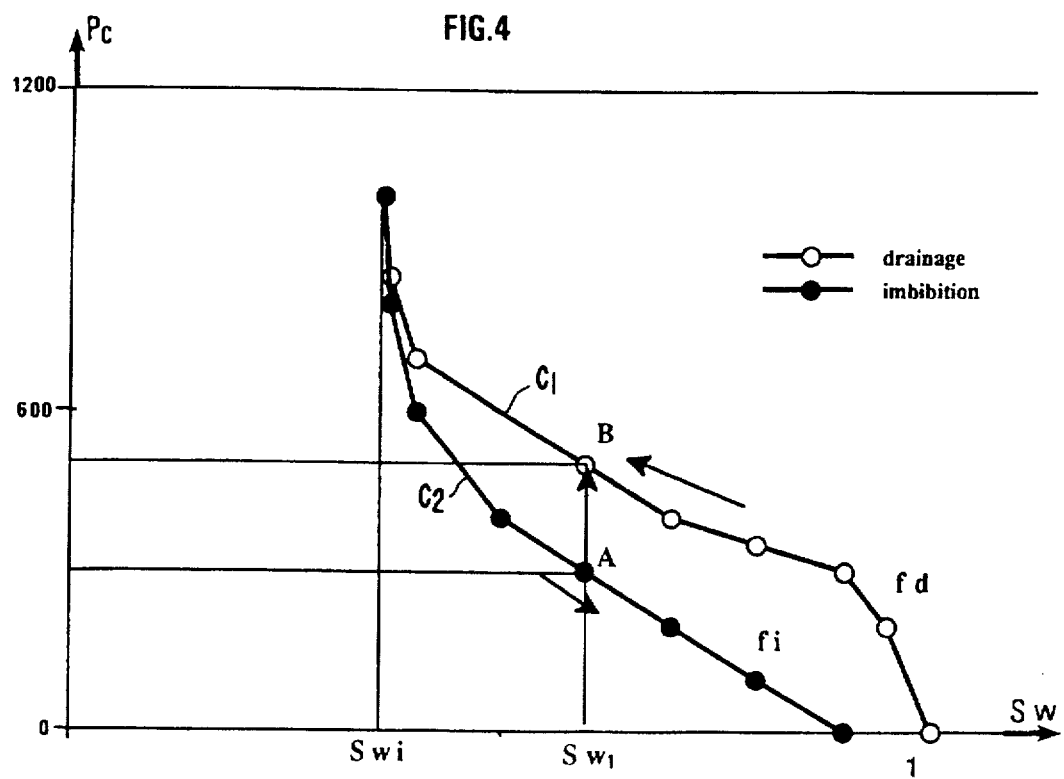
FIG. 4 shows variation curves of the capillary pressure as a function of the wetting fluid saturation of a sample within the scope of three-phase fluid displacement operations.

An important feature of the method consists, when the imbibition starts, in raising the pressure so as to be in the asymptotic part of the curve Pc(So) (FIG. 4). The value of this critical pressure is referred to as Pc (critical pressure). The value of the oil/water differential pressure is checked. Valve 42 being closed, the gas capacity 43 is connected to oil buret 33. The three-way valve 26 is positioned on its gas inlet and two-way valve 27 on its oil inlet.

The cell containing the porous sample is placed horizontally. Valves 29, 38, 51B are closed. The gas is injected through the lateral extensions 5 (FIG. 1) positioned in sleeve 1 in the middle of the cell, through the opening of needle valves 9. The gas pressure is controlled by regulator 47, valves 49A, 49B and valves 51A, 51B are open. The operations to be performed for the three-phase drainage are similar to those defined for a two-phase drainage, the oil being replaced by gas.

Imbibition

In order to obtain a curve of imbibition capillary pressure in the presence of an initial gas saturation, the first two stages are identical to the drainage stages. The oil-water drainage is continued until the irreducible water saturation is reached. The pressure in the oil is then lowered down to the critical pressure. Gas is injected at a pressure corresponding to the desired gas saturation. Needle valves 9 are closed, the two-way valve 26 is positioned on its oil inlet and valve 27 on its water inlet. The oil pressure is raised up to the pressure corresponding to the first oil-water drainage. The imbibition is obtained similarly by decrementing the oil pressure.

We claim:

1. A device for studying a more or less porous material sample in order to determine different physical parameters in connection with fluids consisting of at least two phases, the device comprising a cell for confining a sample including a rigid tubular sleeve and two cell ends positioned at opposite ends of the sleeve, each cell end provided with fastening means for being fastened to the sleeve, an elastic sheath in the cell in which the sample is placed, each cell end being provided with an end portion to be fitted into an end part of the sheath, and with channels connected with means for circulating said fluids through the sample, and pressure means for strongly pressing the sheath around the sample, wherein each cell end comprises a removable cover of a smaller section than the end portion of each cell end allowing access to the opposite ends of the sample during operation, the sheath being kept pressed around the sample by said pressure means.

2. A device as claimed in claim 1, wherein the tubular sleeve comprises at least one tubular extension provided with a radial bore, and means for establishing a connection, through this extension, between the inside of the elastic sheath and a gas supply assembly.

3. A device as claimed in claim 1, wherein the means for circulating said fluids through the sample includes two capillary tubes, respectively, connected to the two opposite ends of the sample through the two cell ends in order to collect two different phases displaced out of the sample, means for injecting the at least two phases respectively through the two opposite ends of the sample, comprising a pump and an injection column, and the gas supply assembly includes a first circuit provided with control means for delivering gas under controlled pressure at the two opposite ends of the two capillary tubes, and a second circuit provided with control means for applying gas under pressure to the injection column to inject a fluid phase into the containment cell, and means for measuring pressure differences between the different phases.

4. A device as claimed in claim 3, wherein the gas supply assembly includes a third circuit provided with control means for injecting gas into the containment cell through at least one tubular extension, for measurements in connection with three-phase fluids, the means for measuring pressure differences between phases comprise a differential pressure detector and multiple-way control valve for connecting selectively said detector to two of the three circuits.

5. A device as claimed in claim 4, wherein the gas supply assembly also includes an injection pressure regulating element and a saturator containing liquid.

6. A device as claimed in claim 1 further comprising a processing assembly for coordinating the circulation of the different phases through the sample and the different circuits.

7. A device as claimed in claim 1, wherein the processing assembly includes a programmed processor, an acquisition card for acquiring pressure measurement signals and a control assembly for controlling selectively the control means on the different circuits.

8. A device as claimed in claim 1 further comprising semipermeable membranes that can be interposed between at least one of the cell ends and one of the ends of the sample.

9. A method for studying a more or less porous material sample in order to determine different physical parameters in connection with a wetting fluid, a nonwetting fluid and a gas, comprising using a cell delimited by a rigid tubular sleeve and two cell ends at the two opposite ends thereof, provided each with means for fastening an end to the tubular sleeve, an elastic sheath in which a sample is placed, and at least one tubular extension provided with a radial bore, means for establishing a connection through the at least one extension, between an inside of the elastic sheath and a gas supply assembly, both cell ends being provided with an end portion to be fitted into an end part of the sheath, with a removable cover of a smaller section than the portion of each cell end allowing access to opposite ends of the sample during operation, and with channels positioned in the cell ends including semipermeable membranes for connection to the means for displacing fluids under pressure through the sample, pressure means for strongly pressing the sheath around the sample, and means for establishing a connection through the tubular sleeve between an inside of the cell and a gas supply assembly, said method comprising performing stages of drainage of the wetting fluid by the nonwetting fluid until an irreducible saturation (Swi) is reached, followed by imbibition stages with the wetting fluid until a determined saturation degree (Sw1) is reached, raising the pressure of the nonwetting liquid while maintaining the determined saturation degree (Sw1) until a determined capillary pressure is obtained, removing at least one of the removable covers for setting at least one gas tight membrane against one end of the sample, and injecting gas by successive increments so as to obtain a displacement of the nonwetting fluid by the gas in the presence of the wetting fluid.

* * * * *